United States Patent [19]

Zhou et al.

[11] Patent Number: 4,794,323
[45] Date of Patent: Dec. 27, 1988

[54] MULTIFUNCTIONAL CERAMIC SENSOR

[75] Inventors: Zhi-Gang Zhou; Zhong-Tai Zhang; Gang Zhao, all of Beijing, China

[73] Assignee: Tsinghua University, Beijing, China

[21] Appl. No.: 846,630

[22] Filed: Apr. 1, 1986

[30] Foreign Application Priority Data

Apr. 1, 1985 [CN] China ................. 85-100146

[51] Int. Cl.$^4$ ............................ G01N 27/12
[52] U.S. Cl. ...................... 324/71.5; 73/23; 73/29; 324/61 R; 324/65 R
[58] Field of Search ............... 324/61 P, 61 R, 65 P, 324/65 R, 437; 73/19, 23, 29, 27 R, 335; 422/98; 338/34

[56] References Cited

U.S. PATENT DOCUMENTS 4,378,691 4/1983 Terada et al. ................ 422/98

OTHER PUBLICATIONS

Chemical Abstracts, vol. 105, #16260g, 1986.

Primary Examiner—A. D. Pellinen
Assistant Examiner—Leon K. Fuller
Attorney, Agent, or Firm—Banner, Birch, McKie & Beckett

[57] ABSTRACT

There is provided a multifunctional ceramic sensor and technology which is capable of detecting temperature, humidity and gas with a single sensing element made of p-type metal-oxide porous ceramic semiconductor Ba($Ti_{1-x}Sn_x$)$O_3$ (x=0.05–0.5). The sensing element is prepared by special ceramic technique which is formed on porosity and sintered on green pack that form a kind of network of capillary pipe with tree-like structure in three dimensions. The present invention posses advantages are as follows: high sensitivity, fast response time, small hysteresis, good separability, high reproducibility and long durability. The multifunctional ceramic sensor not only use for air conditioners, driers, cookers and microwave ovens but also use to detect or control the temperature-humidity-gases for food stuff, tobacco, leather, textile, print, dye and petrochemical industry.

12 Claims, 4 Drawing Sheets

MULTIFUNCTIONAL CERAMIC SENSOR

BACKGROUND OF THE INVENTION

The present invention relates to a multifunctional ceramic sensor and technology with a single sensing element which is capable of detecting temperature, humidity and gas.

Recently, various special sensors have been used to detect the temperature, the humidity or the presence of gases in the surrounding atmosphere which are adapted for use in industry, agriculture, office, family and so on. So that bifunctional ceramic sensor have been developed. The p-type $BaTiO_3$-$SrTiO_3$ and $MgCr_2O_4$-$TiO_2$ used to sense or detect the temperature-humidity and the humidity-gas, respectively. The former has been using as a control device for air conditioners, driers and cookers but the latter for microwave ovens, cookers and roaster etc.

The difficulties of developing such multifunctional sensitive element are as follows. First, the sensitive elements are exposed to the air which contan not only the water vapor but also various gases and oils, this will inevitable cause physical and chemical changes on the sensitive elements, the gases, oil, dust and dirt etc. will adhere to the surfaces of the sensitive elements, whereby the sensitivity would be degraded. Second, the relative humidity is dependent on the temperature of the air varies over a wide range. Almost all of the materials respond to variations in relative humidity, but it is extremely difficult to provide a humidity sensitive element is capable of detecting the relative humidity from 1 to 100% over a wide temperature variation. Third, without the development of materials which are highly responsive to tempeature humidity and gases variations, multifunctional sensors of high reliability. Last but not the least, the multifunctional sensor is capable of detecting temperature-humidity-gas by physical or chemical parameters in the form of electric signals must not exhibite mutual cross-talk.

So far, there has not yet been devised and demonstrated a single sensing element which is capable of sensing trith the temperature-humidity-gas content in the surrounding atmosphere with a reliable degree of accuracy. As a result, the industrial systematization has been much delayed.

SUMMARY OF THE INVENTION

In view of the above, the primary object of the present invention is to provide a multifunctional ceramic sensor which is capable of detecting the temperature, humidity and gas, for instance, propylene, acetylene, ethylene and ethyl alcohol in the surrounding atmosphere.

A multifunctional sensor in accordance with the present invention has a single sensing element is made of a p-type metal-oxide porous ceramic semiconductor. In general, the dielectric constant varies with temperature, the electrical resistance decrease with increase in absorb water vapor, but increase with increase in absorb reducing gases. In other words, the changes in resistance of the p-type semiconductor sensing elements are inversely proportional to their absorption of water vapor but are proportional to their adsorption of reducing gases. Thus they can distinguish between temperature, water vapor and reducing gases in the surrounding atmosphere. It follows that the multifunctional sensing elements are made of p-type semiconductors.

A multifunctional sensor in accordance with the present invention uses a sensing element made of a p-type metal-oxide porous ceramic semiconductor and is capable of sensing the temperature, water vapor and the presence of reducing gases. It is capable of sensing the water vapor in the ion conduction due to the physical absorption of water vapor in its porous structure when the temperature of the sensing element and the ambient temperature are lower than 150° C. And also, it is capable of sensing the presence of reducing gases in terms of variations in electron conduction due to the chemical absorption of reducing gases at temperatures between 200° C. to 550° C. While the physical absorption of water vapor will not occur.

Thus the sensing element in accordance with the present invention can detect the temperature, humidity and gas by electrostatic capacitance and electrical resistance for electric detection.

According to the extensive studies and experiments conducted by the inventors that sensitivity to gas was not too well for $BaTiO_3$-$SrTiO_3$ system, so also sensitivity to temperature was not too well for $MgCr_2O_4$-$TiO_2$ system, and so $BaTiO_3$-$BaSnO_3$ system has been used for substrate of multifunctional ceramic sensing element that made of a p-type metal-oxide porous ceramic semiconductor.

As described previously, the multifunctional ceramic sensor in accordance with the present invention can detect the temperature, humidity and gases with a single sensing element in the surrounding atmopshere. On the other hand, the multifunctional ceramic $BaTiO_3$-$BaSnO_3$ (BTS) sensor in accordance with the present invention has the characteristics of the p-type semiconductor in that the dielectric constant or capacitance decrease with increase in ambient temperatures, the electrical resistance decrease with increase in relative humidity, but increases with increase in the reducing gases content in the surrounding atmosphere. The multifunctional sensing of the present invention can detect temperature range from $-40°$ to $150°$ C., the relative humidity between 1 to 100% and the reducing gases, for instance, propylene, acetylene, ethylene and ethyl alcohol etc. When the multifunctional sensing element are adhered with oils, dust and dirt etc. whereby the sensitivity would be degraded, it can be completely decontaminated by heat-cleaning to temperature higher than 450° C., but the sensing element is fabricated by sintering at high temperatures above 1200° C. as will be described in detail below. It exhibits thermal stable characteristics which are not be degraded or changed when heat-cleaning as described above. Thus the BTS sensing element has a high degree of reproducibility, in functional characteristics, high sensitivity, fast response time, small hysteresis, good separability, high thermal stability and ageinhibility.

A multifunctional sensor in accordance with the present invention make use of separability technique on electrical parameters, frequecnies and temperatures as described previously.

DESCRIPTION OF THE PREFERRED EMBODIMENTS

The present invention will be described in detail with reference to its preferred embodiments, but it is to be understood that the present invention is not limited thereto.

Figure 1:
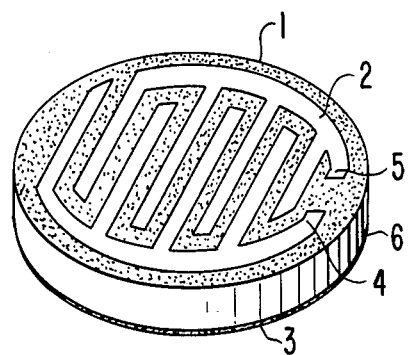
FIG. 1 is a perspective view of a multifunctional porous ceramic sensing element in accordance with the present invention.

In FIG. 1 is shown a multifunctional sensing element in accordance with the present invention. The sensing element consist of substrate [1] electrodes [2] and [3], lead wires, [4], [5] and [6] extended from the electrodes [2] and [3], respectively.

The substrate [1] made of a p-type metal-oxide porous ceramic semiconductor BTS. The interdigital electroes [2] are made of Au and porous electrode layer [3] is made of $RuO_2$. The lead wires 4, 5 and 6 are made of alloy Pt-Ir.

Figure 2:
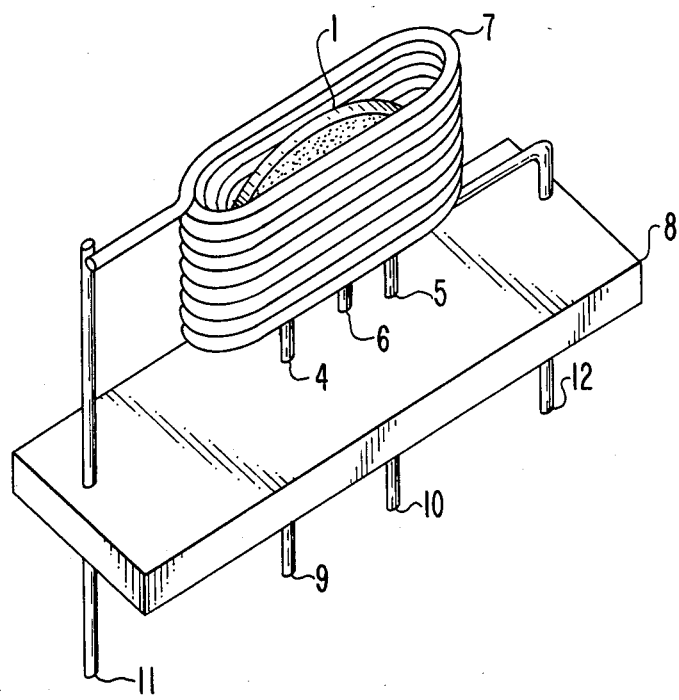
FIG. 2 is a perspective view of a multifunctional sensor incorporating the sensing element shown in FIG. 1.

The sensing element is surrounded by a resistance heating element [7] via lead terminals [9], [10], [11] and [12] that mounted on a base [8] as shown in FIG. 2. The lead wires [4], [5] and [6] through the base [8] connected via lead terminals [9] and [10] to measuring system; the resistance heating element [7] put on the sensing element through the base [8] connected via lead terminals [11] and [12] to a power supply (not shown). Thus a multifunctional sensor is provided.

The substrate [1] is made of a metal-oxide porous ceramics $Ba(Ti_{1-x}Sn_x)O_3$ x=0.05–0.5. It is seen that regardless of the value x, the sensing elements exhibited satisfactory sensitivity to temperature, humidity and gases when the value x exceeds 0.5, sensitivity to temperature drop and resistance to thermal spalling decreases, the value x short of 0.05, sensitivity to gas drop. So that the value x preferably is between 0.05 and 0.50 in practice. One example of the fabrication of the porous ceramic BTS substrate [1] will be described. The raw materials used in preparing the substrate were $BaCO_3$, $SnO_2$ and $TiO_2$ of reagent grade. The weighted powders were completely wet-mixed with pure water and ethyl alcohol by using rubber-lined ball milling containing agate pebbles. After drying, calcined in $BaTiO_3$ and $BaSnO_3$, respectively. The powder mixture with pore-forming additives, for instance, methyl cellulose, ethyl cellulose and polyvinyl alcohol etc. 10 to 60 Vol % of BTS powders, and then formed into porous green disk $\phi$ 6×0.3 mm in size and sintered on green pack in air at temperature between 1200° to 1300° C. for 0.1 to 2h. Thus the porous ceramic substrates [1] are provided. The sizes of pores and porosity of the ceramic substrate [1] can be controlled by amount of pore-forming additives and technology of pore-creating, for instance, the formed and sintered conditions. The porous structure of the substrate posses form a kind of network of capillary pipe with tree-like in three dimensions. The porosity p=25–50%, average grain size $\bar{d}_k < 2$ μm, average pore size $\bar{d}_p < 0.75$ μm.

Figure 3:
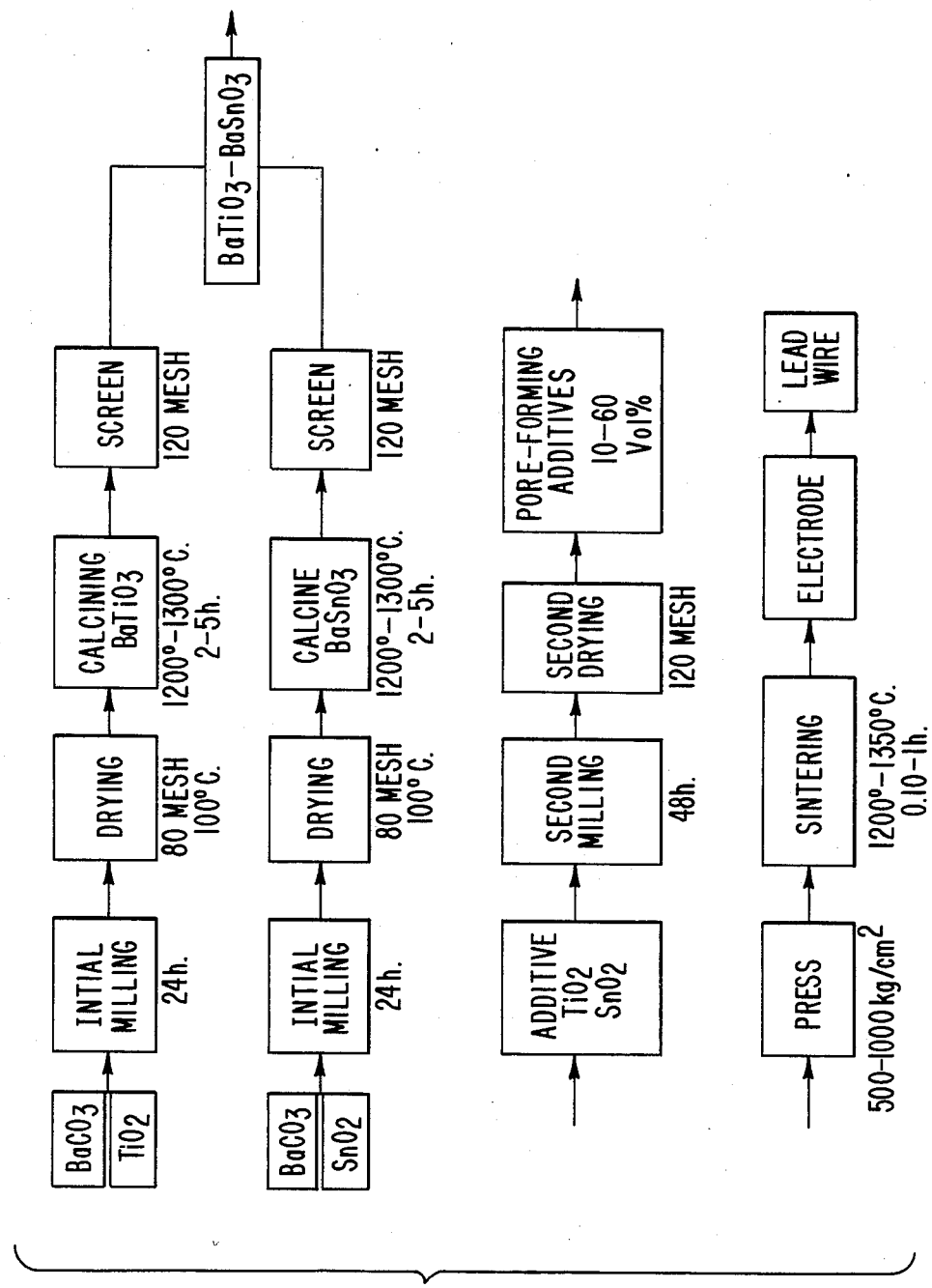
FIG. 3 is a flow chart for multifunctional porous ceramic sensing element in accordance with the present invention.
Figure 4:
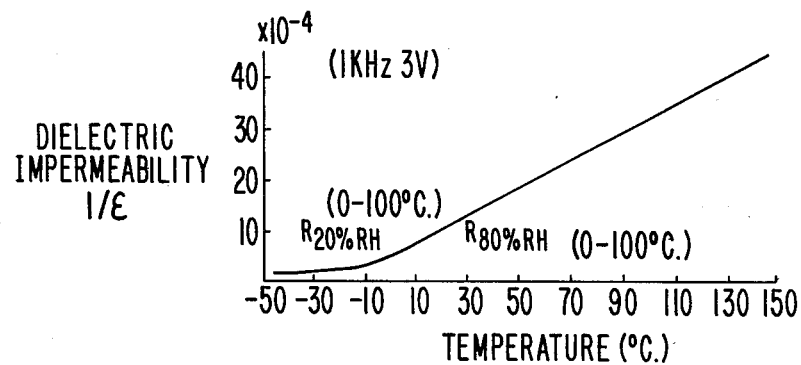
FIG. 4 shows the relationship between the ambient temperature and the bulk electrostatic capacitance of a multifunctional sensing element in accordance with the present invention.
Figure 5:
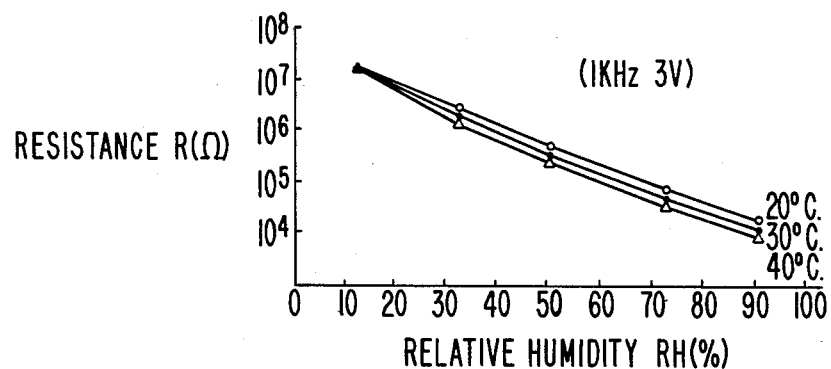
FIG. 5 shows the relationship between the relative humidity and electrical resistance of a multifunctional sensor in accordance with the present invention.
Figure 6:
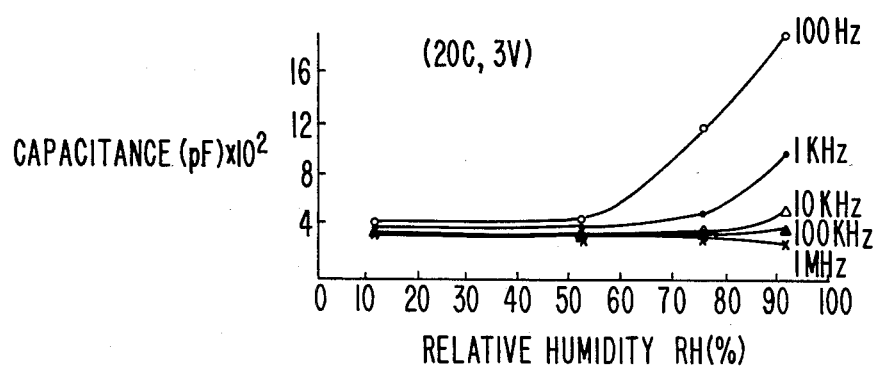
FIG. 6 shows the relationship between the relative humidity, capacitance and frequencies of a multifunctional sensor in accordance with the present invention.
Figure 7:
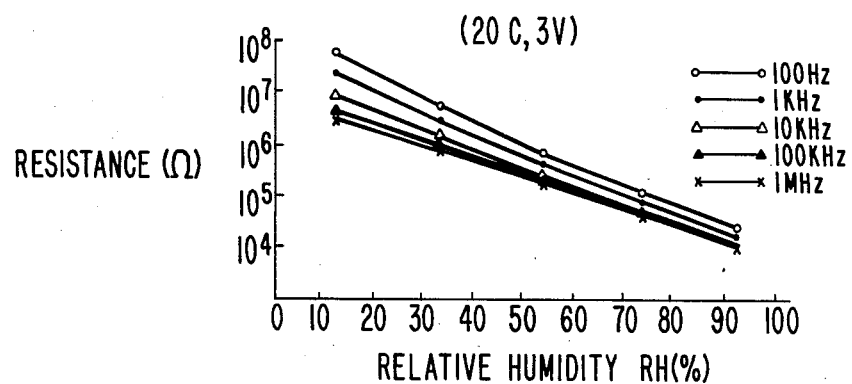
FIG. 7 shows the relationship between the relative humidity, electrical resistance and frequencies of a multifunctional sensor in accordance with the present invention.
Figure 8:
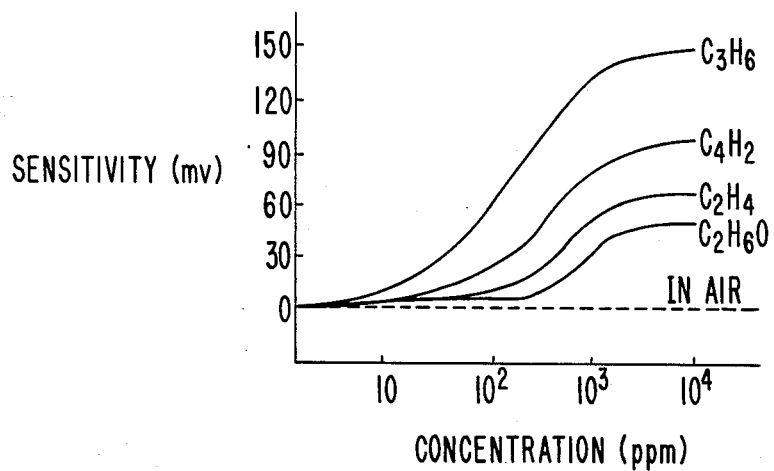
FIG. 8 shows sensitivity of the same sensor to reducing gases in the air in accordance with the present invention.

The interdigital electrodes [2] are made of Au that were vacuum deposited on one of the surfaces of substrate [1]. The porous electrode layer [3] sintered $RuO_2$ paste at 800° C. on the another surface of substrates [1]. The lead wires [4], [5] and [6] are made of Pt-Ir connected by welding with electrode [2] and [3], respectively. After the resistance heating element [7], base [8] and lead terminals [9], [10], [11] and [12] were packed, the multifunctional sensor can detect the temperature, humidity and gases. The flow chart for multifunctional ceramic sensor as shown in FIG. 3.

In order to increase the separability of detectable electrical parameters and decrease mutual crosstalk of electric signals for temperaturehumidity-gases effects may be adopted measures as follows. There are one or more additive dope into main component BTS: as $TiO_2$ (0.1–0.4 wt %), $SnO_2$ (1–4 wt %), perovskite-type, spinels-type, tungsten bronze-type and pyrochlore-type; the temperature were detected at high frequencies (100 KHz–1 MHz), the humidity were detected at low frequencies ($\leq 1$ KHz); the operating temperatures of humidity were $-40°-150°$ C., and also the operating temperatures of gases were 200°–550° C.

The temperature, humidity and gases sensitive characteristics of multifunctional porous ceramic sensing element in accordance with the present invention were as shown in FIGS. 4–8 and TABLE 1.

The multifunctional porous ceramic sensor not only use to detect the temperature-humidity for air conditioners, driers, cookers and microwave ovens but also use to detect or control the temperature-humidity-gases for food stuff, tobacco, leather, textile, print, dye and petrochemical industry. As compared with the single and/or bifunctional ceramic sensor with a single sensing element posses a high sensitivity and selectivity in a certain degree. But there have the advantage over the single and bifunctional ceramic sensor that lead to extend fields of application, brief techniques of detectability, raise efficiencies of detection and lower cost of detector.

EXAMPLE 1

As described previously, the value x of $Ba(Ti_{1-x}Sn_x)O_3$ sensing elements were varied from 0.05 to 0.5. As x=0.22 the composition of the substrate [1] is 0.78 $BaTiO_3 \cdot 0.22$ $BaSnO_3$, dope pore-forming additive methyl cellulose 20 Vol % of ceramic mix, formed into porous green disk at a pressure of 500 kg/cm², sintered in air on green pack at temperature 1230° C. for 10 min. The golden interdigital electrodes [2] were vacuum deposited and the rutherium oxide electrode layer was sintered at 800° C. on both surfaces of the substrate [1], the lead wires [4], [5], [6], the resistance heating element [7], base [8] and lead terminals [9], [10], [11], [12] etc. were described as previously. When the sensor is packed, it can detect the temperature, humidity and gases immediately. The average grain size $\bar{d}_k = 1.5$ μm, average pore size $\bar{d}_p = 0.5$ μm, average specific surface area $\bar{S} = 0.8$ m$^2$/g, total porosity p=35.6% (where open porosity Po=27.6%, close porosity Pc=8%). The porous structure of the substrates [1] posses with tree-like that form a kind of network of capillary pipe in three dimensions.

The multifunctional porous ceramic BTS sensing element in accordance with the present invention can detect the temperature from −40° to 150° C. at frequency 1 MHz, the humidity from 1 to 100% RH at frequency 1 KHz and reducing gases, for instance, propylene, acetylene, ethylene and ethyl alcohol detective limit 10 to 10,000 ppm at 400° C. as shown in TABLE 1.

EXAMPLE 2

As described example 1, the composition of the substrate [1] is 0.78 BaTiO$_3$·0.22 BaSnO$_3$ dope the additive 0.2 wt % TiO$_2$ and 20 Vol % methyl cellulose in accordance with the example 1 that are prepared for multifunctional porous ceramic BTX sensing element, the temperature coefficient of electrical resistance TKR is decreased from $130 \times 10^{-3}$(1/°C.) to $2.5 \times 10^{-3}$(1/°C.) at ambient temperature and lead to the relationship between the dielectric impermeability 1/ε and detective temperature hold to higher linearity. And then the linearity and accuray of temperature-sensitive characteristics are increased as shown in TABLE 2.

EXAMPLE 3

As described example 1, the composition of the substrate [1] is 0.78 BaTiO$_3$·0.22 BaSnO$_3$ dope the additive 1.8 wt % SnO$_2$ and 20 Vol % methyl cellulose in accordance with the example 1 that are prepared for multifunctional porous ceramic BTS sensing element, the sensitivity to humidity α is increased from 1250 to 4020 that compared wtih the undoped but the sensitivity to temperature β is unchanged.

In summary, according to the present invention, the multifunctional porous ceramic BTS sensor can separately detect the temperature, humidity and the concentration of reducing gases in the surrounding atmosphere and is adapted to the mass production.

We claim:

1. A multifunctional ceramic sensor capable of detecting temperature, humidity and gases, said sensor comprising:
    a sensing element formed of a p-type metal-oxide porous ceramic semicondcutor consisting of Ba(Ti$_{1-x}$Sn$_x$)O$_3$ where 0.05<x<0.50;
    said sensing element capable of detecting temperature in accordance with the variations in the dielectric constant of the sensing element with temperature for temperatures from −40° to 150° C., and capable of detecting humidity in accordance with the variations in the electrical resistance of the sensing element with humidity from 1 to 100% RH for temperatures less than 150° C.;
    said sensing element capable of detecting gases in accordance with the variations in the electrical resistance of the sensing element in the presence of gases for temperatures from 200° C. to 550° C.

2. A multifunctional ceramic sensor according to claim 1 wherein said p-type meta-oxide porous ceramic semiconductor is doped with 0.1 to 0.4 wt % TiO$_2$ and 1 to 4 wt % SnO$_2$.

3. A multifunctional ceramic sensor according to claim 1, wherein said p-type metal-oxide porous ceramic semiconductor contains a pore-forming material, sintered to form a network of capillary pipes resembling a tree-like structure in three dimensions, wherein the amount of said pore-forming material is 10–60 vol %, the sintering temperature being 1200°–1350° C.

4. A multifunctional ceramic sensor capable of detecting temperature, humidity and gases, said sensor comprising:
    a sensing element formed of a p-type metal-oxide porous ceramic semiconductor material consisting of Ba(Ti$_{1-x}$Sn$_x$)O$_3$ where 0.05<x<0.50, said sensing element having a dielectric constant which varies in accordance with temperature over a first predetermined range of temperatures and an electrical resistance which varies in accordance with absorbed humidity over a predetermined range of humidities for temperatures less than a predetermined temperature value and which varies in accordance with absorbed gases for temperatures within a second predetermined range of temperatures.

5. A multifunctional ceramic sensor according to claim 4 wherein said first predetermined range of temperatures includes the range −40° to 150° C.

6. A multifunctional ceramic sensor according to claim 4 wherein said predetermined temperature value is 150° C.

7. A multifunctional ceramic sensor according to claim 4 wherein said second predetermined range of temperatures includes the range 200° to 550° C.

8. A multifunctional ceramic sensor according to claim 4 further including heater means for selectively heating said sensing element to a decontamination temperature sufficient to remove adhered contaminates received from the atmosphere.

9. A multifunctional ceramic sensor according to claim 4 further including heater means for selectively heating said sensing element, said heater element being adapted to heat said sensing element to a temperature within said second predetermined range of temperatures.

10. A multifunctional ceramic sensor according to claim 9 wherein said heater means heats said sensing element to a temperature within said second predetermined range of temperatures when detecting the electrical resistance of said sensing element and providing said corresponding gas signal.

11. A multifunctional ceramic sensor according to claim 4 wherein said sensing element includes a substrate formed of said ceramic semiconductor material and interdigital electrodes attached to said substrate, lead wires being attached to said interdigital electrodes and said substrate.

12. A multifunctional ceramic sensor according to claim 4 wherein said sensing element is doped with 0.1 to 0.4 wt % TiO$_2$ and 1 to 4 wt % SnO$_2$.

* * * * *